United States Patent
Nishimoto et al.

(10) Patent No.: US 8,258,348 B2
(45) Date of Patent: Sep. 4, 2012

(54) PROCESS FOR PRODUCTION OF CARBONYL COMPOUND

(75) Inventors: Junichi Nishimoto, Ibaraki (JP); Masayoshi Murakami, Kobe (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 183 days.

(21) Appl. No.: 12/933,074

(22) PCT Filed: Mar. 18, 2009

(86) PCT No.: PCT/JP2009/055319
§ 371 (c)(1),
(2), (4) Date: Sep. 16, 2010

(87) PCT Pub. No.: WO2009/116584
PCT Pub. Date: Sep. 24, 2009

(65) Prior Publication Data
US 2011/0015444 A1 Jan. 20, 2011

(30) Foreign Application Priority Data

| Mar. 19, 2008 | (JP) | P2008-071104 |
| May 20, 2008 | (JP) | P2008-131608 |
| Dec. 16, 2008 | (JP) | P2008-319320 |

(51) Int. Cl.
C07C 45/33 (2006.01)
(52) U.S. Cl. .................... 568/360; 568/401
(58) Field of Classification Search ............ 568/360, 568/401
See application file for complete search history.

(56) References Cited

U.S. PATENT DOCUMENTS

| 4,720,474 A | 1/1988 | Vasilevskis et al. |
| 5,792,721 A | 8/1998 | Grate et al. |
| 6,706,919 B1 | 3/2004 | Obana et al. |

FOREIGN PATENT DOCUMENTS

| DE | 1020060 01 482 A1 | 7/2007 |
| EP | 0 210 705 A1 | 2/1987 |
| EP | 0 498 305 A1 | 8/1992 |
| JP | 59-163335 | 9/1984 |
| JP | 62-033541 | 2/1987 |
| JP | 63-500923 | 4/1988 |
| JP | 5-506853 | 10/1993 |
| JP | 6-091170 | 4/1994 |
| JP | 7-149685 | 6/1995 |
| JP | 2002-265410 | 9/2002 |
| JP | 2007-185656 | 7/2007 |
| WO | WO-87/01615 | 3/1987 |
| WO | WO-01/24924 A1 | 4/2001 |

OTHER PUBLICATIONS

Notification of Transmittal of Translation of the International Preliminary Report on Patentability (IPRP) in PCT/JP2009/055319 dated Nov. 11, 2010.
Communication (Supp EP Search Report) in EP Appln No. 09 72 1736 dated Apr. 15, 2011.
Database WPI, Week 198443, Thomson Scientific, London, GB; AN 1984-266738, XP002631984.
Database WPI, Week 200273, Thomson Scientific, London, GB; AN 2002-679110, XP002631983.
Kishi, A. et al. "Wacker-type oxidation of cyclopentene under dioxygen atmosphere catalyzed by Pd(OAc)$_2$/NPMoV on activated carbon", Tetrahedron Letters, 2000, vol. 41, pp. 99-102.
International Search Report in PCT/JP2009/055319 dated May 19, 2009.

Primary Examiner — Sikarl Witherspoon
(74) Attorney, Agent, or Firm — Foley & Lardner LLP

(57) ABSTRACT

A process for producing a carbonyl compound corresponding to an olefin, the process comprising reacting the olefin with molecular oxygen in a water-containing liquid phase comprising a palladium catalyst, a vanadium compound, and a heteropoly acid having a heteropoly anion represented by the Formula: $[X_a M_b M'_c O_d]^{n-}$ wherein X is any of elements selected from P, Si, and S; a represents an integer of 1 or 2; M and M' represent any of elements selected from Mo, W, V, Ta, and Nb; b and c represent an integer of 0 or more; d represents an integer of 1 or more; and n represents an integer of 1 or more.

7 Claims, No Drawings

PROCESS FOR PRODUCTION OF CARBONYL COMPOUND

TECHNICAL FIELD

The present invention relates to a process for producing a carbonyl compound.

BACKGROUND ART

As a process for producing a carbonyl compound by direct oxidation of an olefine, the Wacker process, which uses a $PdCl_2$—$CuCl_2$ catalyst, has been known for a long time. However, there have been problems with corrosion of equipment by chlorine, by-products containing chlorine compounds, and the like in the Wacker process. Moreover, there are problems that the reaction rate markedly decreases as the carbon number of an olefin material increases and that the reactivity of an internal olefin is low, and the process thus has not been used industrially except in the manufacture of lower carbonyl compounds such as acetaldehyde, acetone, and the like. As a method to resolve these problems, Patent Document 1 discloses a method of carrying out a reaction adding a redox metal under the presence of palladium and a heteropoly acid.
Patent Document 1: Patent Document 1: Japanese Unexamined Patent Application Publication (Translation of PCT Application) No. 63-500923

DISCLOSURE OF THE INVENTION

Problem which the Invention is to Solve

However, this method cannot satisfy the needs from the perspective of productivity because the activity per a unit amount of Pd is low. The present invention provides a process for producing a carbonyl compound, the process having a good activity per a unit amount of Pd and showing excellent productivity.

Means for Solving the Problem

Specifically, the present invention relates to a process for producing a carbonyl compound corresponding to an olefin, the process comprising reacting the olefin with molecular oxygen in a water-containing liquid phase comprising a palladium catalyst, a vanadium compound, and a heteropoly acid having a heteropoly anion represented by the Formula: $[X_aM_bM'_cO_d]^{n-}$
wherein X is any of elements selected from P, Si, and S;
a represents an integer of 1 or 2;
M and M' represent any of elements selected from Mo, W, V, Ta, and Nb;
b and c represent an integer of 0 or more;
d represents an integer of 1 or more; and
n represents an integer of 1 or more.

Effect of the Invention

According to the present invention, carbonyl compounds such as ketone compounds, and the like can be produced in a preferred yield.

BEST MODES FOR CARRYING OUT THE INVENTION

First, the description will be made of a heteropoly acid having a heteropoly anion represented by the Formula: $[X_aM_bM'_cO_d]^{n-}$
wherein, X is any of elements selected from P, Si, and S;
a represents an integer of 1 or 2;
M and M' represent any of elements selected from Mo, W, V, Ta, and Nb;
b and c represent an integer of 0 or more;
d represents an integer of 1 or more; and
n represents an integer of 1 or more.

The upper limit of n is, but not limited to, generally 20, and preferably 10. In the heteropoly anions represented by such a formula, P is particularly preferred for X, and V, Mo, and W are particularly preferred for M and M'.

The composition of typical heteropoly anions includes $XM_xM'_{12-x}O_{40}$, $XM_xM'_{12-x}O_{42}$ wherein x represents an integer satisfying the inequality: $0 \leq x \leq 12$, $XM_yM'_{10-y}O_{34}$ wherein y represents an integer satisfying the inequality: $0 \leq y \leq 10$, $XM_zM'_{11-z}O_{39}$ wherein z represents an integer satisfying the inequality: $0 \leq z \leq 11$, and $X_2M_uM'_{18-u}O_{62}$ wherein u represents an integer satisfying the inequality: $0 \leq u \leq 18$. Specifically, such heteropoly acids include $H_4PV_1Mo_{11}O_{40}$, $H_5PV_2Mo_{10}O_{40}$, $H_3PMo_{12}O_{40}$, $H_3PW_{12}O_{40}$, $H_3PMo_xW_{12-x}O_{40}$ wherein x represents an integer satisfying the inequality: $0<x<11$, $H_6P_2Mo_{18}O_{62}$, and the like.

Besides, the commercially available one itself may be used for the above heteropoly acid, and the acid may be synthesized according to a known method. Additionally, the proton type can also be used for the heteropoly acid, and an acid salt that substitutes any of the protons of the heteropoly acid by an ammonium salt or an alkali metal such as $Na^+$, $K^+$, etc. can also be used. Additionally, a single type of these heteropoly anions may also be used, and these may be used as a mixture of a plurality of the types.

Although a preferred additive amount of the heteropoly acid depends on the type of the heteropoly acid, in many cases, the range of the concentration in a water-containing liquid phase is desirably 0.1 mmol/L to 100 mmol/L, and more preferably 1 mmol/L to 50 mmol/L. The amount of the heteropoly acid is 50 to 0.1 mol per 1 mol of palladium, preferably 20 to 0.5 mol per 1 mol of palladium, and more preferably 1 to 10 mol per 1 mol of palladium.

In the present invention, the vanadium compound is not limited if soluble in the reaction solution, but includes those having a vanadium-oxygen bond such as, for example, $VO_2^+$ and $VO_3^-$, $VO_4^{3-}$, $VO^{2+}$, and the like. Preferably, the compound that can be used is the compound represented by the general formula: $AVO_3$ or $VO(B)_m$ wherein A represents a monovalent cation; B represents an anion; and m represents an integer of 1 or more. The anions represented by B include organic anions such as acetylacetonato and inorganic anions such as sulfate ions, and the specific examples include $NH_4VO_3$, $NaVO_3$, $VOSO_4$, and $(CH_3COCHCOCH_3)_2VO$.

The additive amount of the vanadium compound depends on the type of the heteropoly acid and a vanadium source used, and is preferably 0.5 to 20 g-atm per 1 mol of the heteropoly acid.

The palladium sources that can be used in the present invention include, for example, palladium metals, palladium compounds, and the mixtures thereof.

Examples of the palladium compounds include, for example, organic acid salts of palladium, oxyacid salts of palladium, palladium oxide, and palladium sulfide. In addition, the examples include these salts and oxides, organic or inorganic complexes of the sulfide, and the mixtures thereof.

Examples of the organic acid salts of palladium include, for example, palladium acetate and palladium cyanide. Examples of the oxyacid salts of palladium include, for example, palladium nitrate and palladium sulfate. Examples of these salts and oxides, and organic or inorganic complexes of the sulfide include, for example, tetaaminepalladium (II) nitrate, bis(acetylacetonato)palladium, and the like. Among them, the organic acid salts of palladium or oxyacid salts of palladium are preferred, and palladium acetate is more preferred.

As a water-containing liquid phase of the present invention, water and a water-containing liquid phase in which a suitable organic solvent is added to water can be used. Nitrile compounds are preferred for such an organic solvent, and acetonitrile is preferred among these.

Since the additive amount of the organic solvent depends on the type of an olefin used, the amount cannot be categorically defined, but the preferred ratio by weight of acetonitrile/water is 4.8 to 0.01, and preferably 3 to 0.2 when cyclohexene, for example, is used as an olefin.

In the present invention, the reaction adding palladium, the heteropoly acid, and the vanadium compound can be performed by further adding one or more types of additives, and examples of a particularly preferred additive include iron compounds. Although a known compound can be used as an iron compound, the compounds can include, for example, iron sulfate, iron alum (ammonium iron sulfate), iron nitrate inorganic salts such as iron phosphate, iron citrate, organic acid salts such as iron acetate, iron phthalocyanine, complexes such as iron acetylacetonato, iron oxide, and the like. Among them, the inorganic salts are preferably used, and iron sulfate or iron alum is suitable. The concentration of the preferred iron compound is 0.01 to 100 mol per 1 mol of the heteropoly acid, and more preferably 0.1 to 50 mol per 1 mol of the heteropoly acid.

The olefin that is used in the present invention is not limited, but a cyclic ketone can be obtained efficiently by oxidation of a cyclic olefin in particular. The examples of the cyclic olefin include a cyclic olefin having the carbon number of 4 to 20. These include, for example, cyclobutene, cyclopentene, cyclohexene, cycloheptene, cyclooctene, cyclodecene, cyclododecene, cyclooctadecene, and the like. The cycloolefin that is more preferably used is cyclohexene, and cyclohexanone is produced efficiently from cyclohexene.

Pure oxygen or air can be used as molecular oxygen, and the oxygen may be used as a gas containing molecular oxygen by diluting these gases with an inert gas such as nitrogen, helium, or the like. The amount of oxygen used is usually adjusted by the pressure of the oxygen-containing gas that is injected into a reaction system, and the range of preferably 0.01 to 10 MPa and more preferably 0.05 to 5 MPa as oxygen partial pressure or as gauge pressure is set. This reaction gas, as a total volume, may be injected before reaction, or the reaction may be carried out by continuously supplying the gas, such as by blowing in the system during the reaction, and the like.

The reaction of the present invention is usually carried out under acidic conditions, and the acidity of the solution is desirably adjusted by the additive amount of the heteropoly acid. However, for the case using acid salts of the heteropoly acid and other cases, more preferred reaction results may also be obtained by adjusting the acidity while adding a small amount of another protonic acid.

The protonic acids other than the heteropoly acid include inorganic acids, organic acids, solid acids, and the like, and the inorganic acids include hydrochloric acid, binary acid (hydracid) such as hydrofluoric acid, sulfuric acid, and oxo acid (oxyacid) such as nitric acid. Examples of the organic acids include, for example, formic acid, aliphatic carboxylic acid (e.g., acetic acid), alicyclic carboxylic acid (e.g., cyclohexanecarboxylic acid), aromatic carboxylic acid (e.g., benzoic acid), sulfonic acid, and the like. The sulfonic acid includes, for example, alkyl sulfonic acid (e.g., methanesulfonic acid or ethanesulfonic acid), arylsulfonic acid (e.g., benzenesulfonic acid, p-toluenesulfonic acid or naphthalenesulfonic acid), and the like. Examples of the solid protonic acids include, for example, ion exchange resin (e.g., sulfonic acid-type ion exchange resin, etc.), acidic zeolite and the like, and sulfated zirconia.

For the additive amount of the protonic acid other than the heteropoly acid, the total amount of the separable proton is needed to be adjusted lower than the proton that was contained in the heteropoly acid, and is desirable to be 1/2 or less, and more preferably 1/10 or less.

The reaction is usually performed in a temperature range of 0 to 200° C., preferably 10 to 150° C., and more preferably 30 to 100° C. The reaction is usually performed in a pressure range of 0.01 to 10 MPa (absolute pressure), preferably 0.05 to 7 MPa (absolute pressure), and more preferably 0.1 to 5 MPa (absolute pressure). The reaction can be performed by a batch, a semibatch, a continuous process or the combinations thereof. The catalyst may be added beforehand in a reactor to initiate the reaction, or may be continuously supplied to carry out the reaction.

The reaction solution or reaction gas, both of which contain a product, is collected to isolate a carbonyl compound such as a desired ketone and the like. The produced ketone compound can be separated usually by distillation, phase separation, and the like.

EXAMPLES

Hereinafter, the present invention will be further illustrated in detail by the Examples, but is not limited to the following Examples.

Example 1

The following mixture was placed in a 120-ml autoclave, and was reacted at 323 K for 2 hours under 2 MPa of air and 3 MPa of nitrogen (0.42 MPa of oxygen partial pressure, 4.58 MPa of nitrogen partial pressure) during stirring the mixture with a stirring bar. The obtained reaction mass was analyzed by gas chromatography. The results are shown in Table 1.
(Mixture)
Cyclohexene: 1.6 g (20 mmol),
Solvent: acetonitrile/water (3.0 ml/2.0 ml),
$H_4PV_1Mo_{11}O_{40}$ (manufactured by NIPPON INORGANIC COLOUR & CHEMICAL CO., LTD.): 92 mg (0.04 mmol),
$VOSO_4 \cdot nH_2O$ (KANTO CHEMICAL CO., INC.): 59 mg,
$Pd(OAc)_2$: 4 mg.

Example 2

The reaction was performed in the same manner as Example 1 except that 58 mg of iron alum ($FeNH_4(SO_4)_2 \cdot 12H_2O$, KANTO CHEMICAL CO., INC.) was added. The results are shown in Table 1.

Example 3

The reaction was performed in the same manner as Example 1 except that 33 mg of iron sulfate ($FeSO_4.nH_2O$, Nacalai) was added. The results are shown in Table 1.

Example 4

The reaction was performed in the same manner as Example 3 except that acetonitrile/water (1.5 ml/1.0 ml) was used as a solvent and $VOSO_4.nH_2O$ (KANTO CHEMICAL CO., INC.) was 30 mg. The results are shown in Table 1.

Example 5

The reaction was performed in the same manner as Example 2 except that acetonitrile/water (2.0 ml/3.0 ml) was used as a solvent. The results are shown in Table 1.

Example 6

The reaction was performed in the same manner as Example 2 except that 11 mg of $NaVO_3$ (Nacalai) was used instead of $VOSO_4.nH_2O$. The results are shown in Table 1.

Example 7

The reaction was performed in the same manner as Example 2 except that $H_3PMo_{12}O_{40}$ (NIPPON INORGANIC COLOUR & CHEMICAL CO., LTD.) was used as a heteropoly acid and $VOSO_4.nH_2O$ was 143 mg. The results are shown in Table 1.

Example 8

The reaction was performed in the same manner as Example 6 except that 33 mg of iron sulfate ($FeSO_4.nH_2O$, Nacalai) was added instead of iron alum and acetonitrile/water was 1.5 ml/1.0 ml. The results are shown in Table 1.

Comparative Example 1

The reaction was performed in the same manner as Example 2 except not adding $VOSO_4.nH_2O$. The results are shown in Table 1.

Comparative Example 2

According to a method disclosed in Patent Document 1, $K_5H_4PMo_6V_6Mo_{40}$ was prepared as follows. Specifically, 7.32 g of sodium metavanadate was dissolved into 38 ml of distilled water, and the mixture was kept at 90° C. In addition to this, 8.07 g of sodium molybdate was added to 12 ml of distilled water, and the mixture was heated to 90° C. Then, the above-prepared aqueous sodium metavanadate solution was added thereto. To this mixture was added 5 ml of 85% phosphoric acid. After the mixture was cooled, and stirred during adding 8 g of potassium nitrate, and the solid was then filtrated. The solid was recrystallized from 0.25 M of $H_2SO_4$ to yield $K_5H_4PMo_6V_6O_{40}$.

To acetonitrile/water (1.3 ml/3.8 ml) was added 8 mg of $Pd(NO_3)_2$, 160 mg (0.09 mmol) of prepared $K_5H_4PMo_6V_6O_{40}$, and 120 mg of $Cu(NO_3)_2.3H_2O$, and further added 7.7 mg (0.08 mmol) of sulfuric acid. Then, 210 mg (2.6 mmol) of cyclohexene was added thereto. The mixture was placed in a 120-ml autoclave, and was reacted at 323 K for 2 hours under 2 MPa of air and 3 MPa of nitrogen (0.42 MPa of oxygen partial pressure, 4.58 MPa of nitrogen partial pressure) during stirring with a stirring bar. Table 1 shows the results in which the obtained reaction mass was analyzed by gas chromatography.

TABLE 1

| | Heteropoly acid | Vanadium compound | Iron compound | Conversion rate | Cyclohexanone selectivity | TOF ($h^{-1}$) | Acetamide/ Cyclohexanone (mol %) |
|---|---|---|---|---|---|---|---|
| Example 1 | $H_4PV_1Mo_{11}O_{40}$ | $VOSO_4$ | — | 14 | 78 | 69 | 0.0 |
| Example 2 | $H_4PV_1Mo_{11}O_{40}$ | $VOSO_4$ | Iron alum | 38 | 95 | 209 | 1.0 |
| Example 3 | $H_4PV_1Mo_{11}O_{40}$ | $VOSO_4$ | Iron sulfate | 24 | 96 | 132 | 1.9 |
| Example 4 | $H_4PV_1Mo_{11}O_{40}$ | $VOSO_4$ | Iron sulfate | 24 | 97 | 126 | 1.5 |
| Example 5 | $H_4PV_1Mo_{11}O_{40}$ | $VOSO_4$ | Iron alum | 32 | 95 | 162 | 2.1 |
| Example 6 | $H_4PV_1Mo_{11}O_{40}$ | $NaVO_3$ | Iron alum | 28 | 96 | 138 | 1.5 |
| Example 7 | $H_3PMo_{12}O_{40}$ | $VOSO_4$ | Iron alum | 25 | 96 | 126 | 0.0 |
| Example 8 | $H_3PMo_{12}O_{40}$ | $VOSO_4$ | Iron sulfate | 22 | 95 | 118 | 4.0 |
| Comparative Example 1 | $H_4PV_1Mo_{11}O_{40}$ | — | Iron alum | 2 | 78 | 10 | 0.0 |
| Comparative Example 2 | $K_5H_4PMo_6V_6O_{40}$ | — | Copper nitrate | 23 | 73 | 7 | 119 |

In Table 1, the conversion rate represents the conversion rate of cyclohexene, and TOF ($h^{-1}$) means (number of moles generated for cyclohexanone)/(number of moles of Pd)/(reaction time). Acetamide/Cyclohexanone (mol %) represents the ratio between generated cyclohexanone and acetamide.

INDUSTRIAL APPLICABILITY

The present invention can be a useful process for producing a carbonyl compound such as cyclohexanone.

The invention claimed is:
1. A process for producing a carbonyl compound corresponding to an olefin, the process comprising reacting the olefin with molecular oxygen in a water-containing liquid phase comprising a palladium catalyst, a vanadium compound, and a heteropoly acid having a heteropoly anion represented by the Formula: $[X_aM_bM'_cO_d]^{n-}$ wherein X is any of elements selected from P, Si, and S;
a represents an integer of 1 or 2;
M and M' represent any of elements selected from Mo, W, V, Ta, and Nb;
b and c represent an integer of 0 or more;
d represents an integer of 1 or more; and
n represents an integer of 1 or more.

2. The process according to claim 1, wherein the vanadium compound is a vanadium compound represented by the formula: $AVO_3$ or $VO(B)_m$
wherein A represents a monovalent cation;
B represents an anion; and
m represents an integer of 1 or more.

3. The process according to claim 1, wherein the water-containing liquid phase is a water-containing liquid phase containing an organic solvent.

4. The process according to claim 1, wherein the water-containing liquid phase is a water-containing liquid phase containing acetonitrile.

5. The process according to claim 1, wherein the olefin is a cyclic olefin and the carbonyl compound is a cyclic ketone.

6. The process according to claim 1, wherein the olefin is cyclohexene and the carbonyl compound is cyclohexanone.

7. The process according to claim 1, wherein the reaction is performed in the presence of an iron compound.

* * * * *